(12) United States Patent
Paulussen et al.

(10) Patent No.: US 10,548,491 B2
(45) Date of Patent: Feb. 4, 2020

(54) PHOTOPLETHYSMOGRAPHY APPARATUS

(71) Applicant: KONINKLIJKE PHILIPS N.V., Eindhoven (NL)

(72) Inventors: Elvira Johanna Maria Paulussen, Eindhoven (NL); Cristian Nicolae Presura, Veldhoven (NL); Edgar Martinus van Gool, Veghel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 137 days.

(21) Appl. No.: 15/546,344

(22) PCT Filed: Jan. 26, 2016

(86) PCT No.: PCT/EP2016/051495
§ 371 (c)(1),
(2) Date: Jul. 26, 2017

(87) PCT Pub. No.: WO2016/120229
PCT Pub. Date: Aug. 4, 2016

(65) Prior Publication Data
US 2018/0014737 A1    Jan. 18, 2018

(30) Foreign Application Priority Data
Jan. 30, 2015  (EP) .................................. 15153307

(51) Int. Cl.
*A61B 5/024* (2006.01)
*A61B 5/1455* (2006.01)
(Continued)

(52) U.S. Cl.
CPC ...... *A61B 5/02427* (2013.01); *A61B 5/14552* (2013.01); *A61B 8/54* (2013.01); *G02B 26/127* (2013.01); *A61B 2562/0242* (2013.01)

(58) Field of Classification Search
CPC ... A61B 5/02427; A61B 8/54; A61B 5/14552; A61B 5/0037; A61B 5/14551; A61B 5/02416; A61B 2562/0242; G02B 26/127
See application file for complete search history.

(56) References Cited

U.S. PATENT DOCUMENTS

2004/0024326 A1  2/2004  Yeo et al.
2006/0247507 A1* 11/2006  Ruiter .................. A61B 5/1495
                                                        600/331
(Continued)

FOREIGN PATENT DOCUMENTS

EP    2438849 A1    4/2012
EP    2687154 A1    1/2014
(Continued)

OTHER PUBLICATIONS

Wijshoff, et al., "Reducing motion artifacts in photoplethysmograms by using relative sensor motion: phantom study", Journal of Biomedical Options, vol. 17(11), Nov. 2012, pp. 117007-1 thru 117007-15.

*Primary Examiner* — Eric F Winakur
*Assistant Examiner* — Abid A Mustansir

(57) ABSTRACT

The invention relates to a photoplethysmography (PPG) apparatus (100), comprising at least one light source (110) configured to generate a beam of source light (114) having a source beam angle (118) and at least one controllable beam angle adapter (120) configured to receive a beam-angle control signal (170) indicative of a modified beam angle (124) to be set, the beam angle adapter (120) being further configured to provide the beam of source light (114) with a modified beam angle (124) to an external object (130). The PPG apparatus (100) comprises at least one PPG sensor (140)configured to provide a sensor signal (145) indicative of source light (150) scattered by the external object (130), and a PPG evaluation and control unit (160) configured to (Continued)

receive the sensor signal (145), to provide the beam-angle control signal (170) and to provide at its output (180) an AC signal component of the sensor signal (145).

14 Claims, 5 Drawing Sheets

(51) Int. Cl.
*A61B 8/00* (2006.01)
*G02B 26/12* (2006.01)

(56) References Cited

U.S. PATENT DOCUMENTS

| | | |
|---|---|---|
| 2007/0139792 A1 | 6/2007 | Sayag |
| 2007/0270699 A1 | 11/2007 | Crabtree et al. |
| 2008/0275322 A1* | 11/2008 | Kim .................. A61B 5/14552 |
| | | 600/324 |
| 2009/0082642 A1 | 3/2009 | Fine |
| 2010/0056880 A1 | 3/2010 | Cho et al. |
| 2014/0121471 A1 | 5/2014 | Walker |
| 2014/0155759 A1 | 6/2014 | Kaestle et al. |
| 2014/0200423 A1 | 7/2014 | Eisen et al. |
| 2014/0253709 A1 | 9/2014 | Bresch et al. |
| 2014/0336479 A1* | 11/2014 | Ando .................. A61B 5/4041 |
| | | 600/310 |

FOREIGN PATENT DOCUMENTS

| | | |
|---|---|---|
| WO | 9313706 A2 | 7/1993 |
| WO | 2014136027 A1 | 9/2014 |

\* cited by examiner

PHOTOPLETHYSMOGRAPHY APPARATUS

This application is the U.S. National Phase application under 35 U.S.C. § 371 of International Application No. PCT/EP2016/051495, filed on Jan. 26, 2016, which claims the benefit of European Application No. 15153307.2, filed Jan. 30, 2015. These applications are hereby incorporated by reference herein.

FIELD OF THE INVENTION

The invention relates to a photoplethysmography apparatus, to a method for operating a photoplethysmography apparatus, and to a computer program for operating a photoplethysmography apparatus.

BACKGROUND OF THE INVENTION

A photoplethysmography (PPG) apparatus measures changes in the volume of an external object in an optical way. In medical applications, these changes in volume usually are changes of the amount of blood or air in an organ or other body part of a subject and can therefore be used to monitor vital-sign information of the subject. Vital-sign information of a subject comprises for instance information on respiratory rate, pulse rate, blood pressure, or blood oxygen saturation of a person.

In WO 2014/136027 A1, also published under U.S. 2014/0253709A1, a system and method for determining vital-sign information of a subject is disclosed. The subject is illuminated with radiation, and radiation reflected from the subject is received. In a first phase, a region of interest is located. In a second phase, the illumination is controlled to locally illuminate the located region of interest. Finally, vital-sign information of the subject is determined from the radiation reflected from the region of interest and detected in said second phase.

SUMMARY OF THE INVENTION

According to a first aspect of the present invention, a photoplethysmography apparatus is provided, hereinafter PPG apparatus, comprising
- at least one light source configured to generate a beam of source light having a source beam angle directed towards an external object;
- at least one controllable beam angle adapter arranged between the light source and the external object and configured to receive a beam-angle control signal indicative of a modified beam angle to be set, which differs from the source beam angle, the beam angle adapter being further configured to receive the beam of source light having the source beam angle and to provide the beam of source light with the modified beam angle to the external object;
- at least one PPG sensor which is arranged and configured to provide a sensor signal indicative of scattered source light, which has been scattered by the external object and detected by the PPG sensor; and
- a PPG evaluation and control unit, which is configured to receive the sensor signal, to provide the beam-angle control signal and to determine and selectively provide at its output an AC signal component of the sensor signal wherein the PPG evaluation and control unit is further configured to determine and provide the beam-angle control signal in dependence on a DC signal component of the sensor signal or on the AC signal component of the sensor signal or in dependence on both.

The PPG apparatus of the present invention is based on the recognition that a modification of the source beam angle of the source light can lead to a significant improvement of the sensor signal. In the PPG apparatus of the present invention, the source beam angle of the beam emitted by the light source can be modified by the at least one beam angle adapter. Control of the beam-angle adaptation is provided by the PPG evaluation and control unit providing the beam-angle control signal. Enabling a modification of the source beam angle allows improving the sensor signal in response to optical characteristics of a particular external object under investigation and in response to particular conditions of the PPG measurement. Providing such modification capability of the source beam angle therefore not only improves the signal for a given external object and circumstances of PPG measurement, but also extends the field of application cases for the PPG apparatus. For instance, as will be explained in more detail further below, the PPG apparatus can be used to provide high-quality PPG information for a particularly wide range of external objects in a particularly wide range of conditions, extending to measurement under relative motion between the external object and the PPG apparatus etc. Hence, the PPG apparatus can be adapted to different external objects or to different environments.

Since all components of the PPG apparatus can be provided in small extents, the PPG apparatus itself can also have a small size.

It is noted for clarification that the external object does not form a part of the claimed PPG apparatus. The external object is the object which is to be investigated by the PPG apparatus and thus can be changed arbitrarily. Non-limiting examples of external objects are elastic tubes, animals, and human beings.

The AC (amplitude change) signal component of the sensor signal comprises information on a change of detected scattered source light intensity as a function of time. This change is at least in part caused by a change of the volume or of the surface of the external object.

In the following, embodiments of the PPG apparatus will be described.

In one embodiment of the PPG apparatus, the beam angle adapter comprises a liquid crystal element, in particular, a liquid crystal lens with an adjustable focal length. In a variant of this embodiment, the beam angle adapter further comprises a driver circuit for setting a focal length of the liquid crystal lens in response to the beam-angle control signal. In a further embodiment, the beam angle adapter comprises a liquid element, in particular a liquid lens. In a liquid lens, the modifying of the source beam angle by the beam angle adapter is for instance effected by a change of a surface tension of the liquid lens by a driver circuit in response to the beam-angle control signal.

There are different options to determine the modified beam-angle. A first group of embodiments does not rely on user input.

In one embodiment of this first group of embodiments, the PPG evaluation and control unit is further configured to determine and provide the beam-angle control signal in dependence on a DC signal component of the sensor signal. Since the DC signal component of the sensor signal includes an intensity of source light reflected or transmitted without further interaction with the external object received by the PPG sensor, this can be used as a control measure in order to determine whether or not a sufficient amount of scattered source light reaches the PPG sensor. Another option is to use the DC component for optimizing the AC component, based on a known dependence of a ratio of the AC and DC signal components on an amount of the DC signal component. Based on such information provided by the DC signal component of the sensor signal, the beam-angle control signal can be adapted to adjust the beam angle of the beam of source light.

In another embodiment of the first group, the PPG evaluation and control unit is configured to determine and provide the beam-angle control signal in dependence on the AC signal component of the sensor signal. This embodiment achieves, for instance, when a weak AC signal component is detected, that the beam-angle adapter is controlled to adapt the modified beam angle until a sufficient amount of the AC signal component is detected.

In a further embodiment of the first group, the PPG evaluation and control unit is configured to determine and provide the beam-angle control signal in dependence on the AC signal component and in additional dependence on the DC signal component of the sensor signal. In one variant of this embodiment, the beam-angle control signal depends on a ratio of the AC and the DC signal components of the sensor signal.

In another embodiment of the first group, the PPG evaluation and control unit is configured to determine a ratio difference between a ratio of the AC signal component of the sensor signal and the DC signal component of the sensor signal and a predetermined reference ratio thereof, and to provide the beam-angle control signal in dependence on the ratio difference. In this embodiment, the PPG apparatus changes the source beam angle to set a modified beam angle until the ratio difference vanishes or is smaller than a predetermined ratio-difference threshold, which means that the ratio of the AC and DC signal component is close to the predetermined reference ratio.

In a further embodiment of the first group, the PPG apparatus comprises a distance sensor, which is configured to provide a distance signal which is indicative of a distance between the light source and the external object. In this embodiment, the PPG evaluation and control unit is preferably configured to receive the distance signal and to determine and provide the beam-angle control signal in dependence on the received distance signal. As an example, in one variant of this embodiment, a larger detected distance between the light source and the external object leads to the beam-angle control signal corresponding to a smaller beam angle at the output of the beam-angle adapter. The distance sensor may be provided in one of many different ways, which are known per se. In one variant, the distance sensor is configured to determine the distance by a time-of-flight measurement (TOA, TDOA) for a pulse of electromagnetic radiation provided by the distance sensor and backscattered by the external object. The distance may be measured in an alternative variant by mechanical means, for example by a measuring an extension or a force using a spring with a tip touching the external object.

As mentioned, an advantage of this group of embodiments is that the PPG apparatus can set the modified beam angle to achieve an optimized sensor signal without any user input at the time of measurement.

In another embodiment, the PPG apparatus comprises a pressure sensor, which is configured to provide a pressure signal indicative of a pressure exerted by the PPG apparatus on the external object; wherein the PPG evaluation and control unit is configured to receive the pressure signal and to determine and provide the beam-angle control signal in dependence on the received pressure signal. In a variant of this embodiment, the pressure sensor comprises a piezo-electric circuit providing a pressure dependent voltage. In variants of this embodiment, an increasing pressure exerted by the PPG apparatus on the external object leads to a decreasing modified beam angle and to a corresponding beam-angle control signal. In a further variant of this embodiment, the PPG apparatus is installed into the encasement of a watch and the pressure is exerted by the watch on an arm of the user, while the user is the external object.

In a second group of embodiments of the PPG apparatus, the PPG evaluation and control unit is further configured to receive beam-angle control information as a user input via a user input interface of the PPG apparatus and to determine and provide the beam-angle control signal in dependence on the beam-angle control information. In one variant of this embodiment, the beam-angle control information provided by a user is the only information used to determine the beam-angle control signal, which means that the user controls the modified beam angle. In a further variant of this embodiment, the beam-angle control information provided by the user includes a parameter value pertaining to the external object, which allows setting the modified beam angle in correspondence to the provided parameter value.

Any user input may be provided via a user input interface, which in different exemplary and non-limiting variants is formed by a stationary computer, a mobile phone, a notebook computer, a computer watch device, or a convertible or tablet computer.

In a further embodiment of the PPG apparatus, the PPG evaluation and control unit is configured to control performance of a calibration measurement by the PPG apparatus to provide a calibration of the PPG apparatus. The calibration provides an allocation of the DC signal component of the sensor signal or of a signal-component ratio of the AC signal component of the sensor signal and the DC signal component of the sensor signal to an object type by a predetermined object-type classification of external objects. The object-type classification allocates different amounts of the DC signal component or of the signal-component ratio to different object types.

In application cases forming variants of this embodiment, which may be combined with each other to form further variants, object type classifications differentiate between different skin colors, different stages of skin age, different skin temperatures or different degrees of skin moisture. In variants of this embodiment, a calibration of the PPG apparatus achievable with the calibration measurement provides an allocation of the DC signal component and the modified beam angle to the object-type classification, while the object-type classification further allocates different amounts of the DC signal component and different modified beam angles to the different object types.

In performing the calibration measurement, the PPG apparatus is preferably configured to additionally measure a distance between the light source and the external object. In another variant of this embodiment, the PPG apparatus is configured to additionally measure a pressure exerted by the PPG apparatus on the external object, for instance using an integrated pressure sensor, as a calibration pressure for the calibration measurement, comprising a pressure dependent object-type classification. A suitable modified beam angle is thus determined by the PPG evaluation and control unit according to the allocation of the object type to a suitable beam angle by a predetermined allocation scheme between object types and suitable beam angles.

In one embodiment of the PPG apparatus, the PPG evaluation and control unit is configured to determine an object type based on the sensor signal and the calibration, and to determine the beam-angle control signal in dependence on the object type determined in the calibration. Thus, the PPG evaluation and control unit performs the calibration measurement, in this way determines the object type of the external object and can therefore provide the beam-angle control signal which is indicative of a suitable modified beam angle of the beam of source light with respect to the determined object type. Thus, the PPG evaluation and control unit is configured to adapt the beam-angle control signal to the external object without any user input.

In another embodiment of the PPG apparatus, the PPG evaluation and control unit is further configured to determine at least one motion parameter indicative of a motion of the external object as a whole relative to the light source, and to determine the beam-angle control signal in dependence on the motion parameter. In this embodiment, the beam angle of the light source is adapted to the motion of the external object which helps reducing undesired motion artifacts in the sensor signal of the PPG sensor. In a variant of this embodiment, the motion parameter is determined based on two distance signals determined by the distance sensor at different points in time. A motion to be estimated may be the motion of the external object relative to the light source of the PPG apparatus along the propagation direction of the beam of source light. Adapting the modified beam angle based on the motion parameter can for example comprise decreasing the source beam angle in response to a determined motion that increases a distance between the light source and the external object. Analogously, a decreasing distance between the light source and the external object according to the motion parameter may leads to an increased modified beam angle in comparison with the source beam angle, controlled by the corresponding beam-angle control signal.

In a further variant of this embodiment comprising motion estimation, the PPG apparatus is additionally configured to be attached to the external object and comprises a linear acceleration sensor for detecting acceleration in at least one direction which is configured to provide an acceleration signal indicative of a common motion or acceleration of the PPG apparatus and the external object. This allows further reducing motion artifacts in the sensor signal by suitably controlling the modified beam angle.

In a further embodiment, the PPG apparatus comprises a user output interface which is configured to provide an output indicative of the AC signal component of the sensor signal, or of the DC signal component of the sensor signal, or of the beam-angle control signal, or any information derivable from such signal components or signals. In a variant of this embodiment of the PPG apparatus, the output is a graphical signal on a display of the output interface. In other variants of this embodiment, the output is an acoustic signal or a single LED signal.

In a further embodiment of the first aspect of the invention, the PPG apparatus comprises a memory unit configured to save beam-angle control signals. In a variant of this embodiment, previous beam-angle control signals saved in the memory unit are taken into account when determining a current beam-angle control signal.

In a further embodiment, the PPG apparatus comprises a distance adaptation device, configured to receive a distance control signal and to modify the distance between the light source and the external object in dependence on the distance control signal. Such a distance adaptation device can set a predetermined distance between the light source and the external object prior to the PPG measurement in order to enable the PPG evaluation and control unit to determine the beam-angle control signal based on this known distance value, in particular with reference to a calibration of the PPG apparatus provided for this distance value. Preferably, the PPG evaluation and control unit of this embodiment is further configured to receive a current distance value as distance control information and to determine the distance control signal based on this distance control information. In one variant of this embodiment, the distance adaptation device is a mechanism for changing the position of the light source, for example using a thread or a cogwheel or a piezoelectric positioning element.

The PPG apparatus of one embodiment is configured for detection of the source light in a back-scattering mode of operation. In another embodiment, the PPG apparatus is configured for detection of the source light in a transmission mode of operation.

A further embodiment of the PPG apparatus comprises an encasement arranged to encase at least the light source, the PPG evaluation and control unit, the beam angle adapter and the PPG sensor, thus providing a carrying device for the PPG apparatus. In variants of this embodiment, the carrying device is a grasp, or a wristband, or a watchstrap or a clip.

In one embodiment of the PPG apparatus, the light source is a light emitting diode (LED). In a variant of this embodiment, the beam of source light emitted by the LED is collimated, for example by a lens. In another embodiment, the light source is a laser source, in particular a laser diode.

Typically, the LED or the laser source has a characteristic wavelength used for the PPG measurement. In one variant of the PPG apparatus, the light source comprises two LEDs or two laser sources with a first and a second characteristic wavelength, differing from each other. These characteristic wavelengths enable the PPG evaluation and control unit to receive a first and a second sensor signal and to compare both, according to possibly different absorption characteristics of the external object, by determining an AC-signal ratio between a first AC signal component of the first sensor signal and a second AC signal component of the second sensor signal.

The PPG sensor is typically a photodiode, but can also be any other light-sensitive detector device, including a CCD sensor, or a video camera.

In some embodiments, the PPG evaluation and control unit is separated into an evaluation part and into a control part, and the evaluation part and the control part are spatially separated within the PPG apparatus. In other embodiments, PPG evaluation and control unit is a single hardware unit, which may for instance be implemented by a programmable microcontroller or microprocessor.

According to a second aspect of the present invention, a method for operating a PPG apparatus comprises
  providing at least one beam of source light having a source beam angle directed towards an external object;
  determining and providing a beam-angle control signal indicative of a modified beam angle to be set, which differs from the source beam angle of the at least one beam of source light;
  adapting the at least one beam of source light in dependence on the beam-angle control signal to set the modified beam angle by means of at least one beam angle adapter;
  providing a sensor signal indicative of scattered source light, which has been scattered by the external object; and determining and selectively providing an AC signal component of the sensor signal;
wherein
determining and providing the beam-angle control signal is performed in dependence on a DC signal component of the sensor signal or on the AC signal component of the sensor signal or in dependence on both.

The method of the second aspect of the invention shares the advantages described in the context of the PPG apparatus of the first aspect.

Some embodiments of the method further comprise providing a distance signal which is indicative of a distance between the light source and the external object, or providing a pressure signal which is indicative of a pressure exerted by the PPG apparatus on the external object. Furthermore, said embodiments may additionally comprise receiving the distance signal or the pressure signal and determining and providing the beam-angle control signal in dependence on the received distance signal or pressure signal.

In further embodiments according to the second aspect of the invention, the method for operating a PPG apparatus further comprises as a first step the providing of an allocation of a DC signal component of the sensor signal or of a signal-component ratio of the AC signal component of the sensor signal and the DC signal component of the sensor signal to an object type by a predetermined object-type classification of external objects. The object-type classification allocates different amounts of the DC signal component or of the signal-component ratio to different object types. As a second step, this method comprises the determining of the beam-angle control signal in dependence on the object type determined by the allocation. In a variant of this embodiment, the PPG evaluation and control unit determines as a result of the calibration measurement the object type according to the object-type classification and furthermore determines a suitable modified beam angle by using a second allocation of the object type to the suitable modified beam angle, and provides the corresponding beam-angle control signal.

A further embodiment of the method for operating a PPG apparatus comprises determining at least one motion parameter from a sequence of at least two sensor signals taken at different points in time. The at least one motion parameter is thus indicative of a motion of the external object as a whole relative to the light source. This allows determining the beam-angle control signal in dependence on the motion parameter.

According to a third aspect of the present invention, a computer program for operating a PPG apparatus comprises program code means for causing a computer to carry out a method according to the second aspect of the invention.

The computer which comprises the computer program may for instance form an integrated part of a computer watch device and be implemented as a microcontroller or microprocessor. In another embodiment, the computer forms an integrated part of a hospital computer system. In yet another embodiment, the computer is integrated into a medical device and the computer program comprises program code means for determining vital sign information, such as respiratory rate, pulse rate, blood pressure, blood volume fraction and oxygen saturation from the sensor signal of the PPG apparatus.

It shall be understood that the PPG apparatus of the first aspect of the invention, also defined in claim 1, the method for operating a PPG apparatus of the second aspect, also defined in claim 11, and the computer program for operating a PPG apparatus, also defined in claim 15, have similar and/or identical embodiments.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
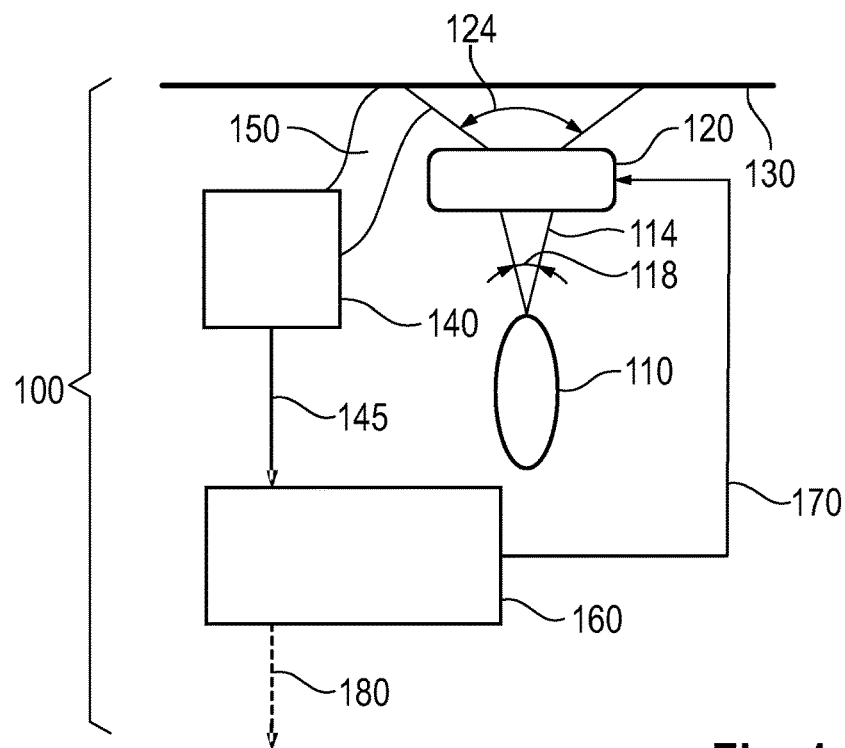
FIG. 1 shows a block diagram of an embodiment of a PPG apparatus.

FIG. 1 shows a simplified block diagram of an embodiment of a PPG apparatus 100. The PPG apparatus 100 comprises a light source 110, which provides a beam of source light 114 with a source beam angle 118. The beam of source light 114 has the form of a cone of light and therefore comprises an opening angle of said cone of light. The source beam angle 118 is the opening angle of the beam of source light 114 between the light source 110 and a PPG beam angle adapter 120.

The controllable beam angle adapter 120 is arranged between the light source 110 and an external object 130 and is configured to receive the beam of source light 114 having the source beam angle 118 and to provide the beam of source light 114 with a modified beam angle 124 to the external object 130. The modified beam angle 124 is the opening angle of the beam of source light 114 between the PPG beam angle adapter 120 and the external object 130.

The PPG apparatus 100 furthermore comprises a PPG sensor 140 which is arranged and configured to provide a sensor signal 145 indicative of scattered source light 150, which has been scattered by the external object 130 and detected by the PPG sensor 140. A PPG evaluation and control unit 160 is configured to receive the sensor signal 145, to provide the beam-angle control signal 170 and to determine and selectively provide at its output 180 an AC signal component of the sensor signal 145.

The beam-angle control signal 170 is indicative of a modified beam angle to be set and is received by the beam angle adapter 120, which sets the modified beam angle 124 according to the beam-angle control signal 170. The modified beam angle 124 is changed in order to improve an evaluation of the sensor signal 145. Hence, control of a beam-angle adaptation is provided by the PPG evaluation and control unit 160 and therefore the PPG apparatus 100 can be adapted to different external objects 130 or to different environments.

The output 180 of the PPG apparatus 100 is in this embodiment an AC signal component of the sensor signal 145. The AC signal component of the sensor signal 145 gives a measure for the rate of change and for the absolute change of light intensity within the sensor signal 145 due to a change of the volume or the surface of the external object 130. Thus, the PPG apparatus 100 provides a non-invasive measuring of changes in the volume or the surface of an external object 130 and therefore provide an output 180 which can be indicative of vital sign information of the external object 130, for example a human being, such as respiratory rate, pulse rate and blood pressure.

The light source 110 in this embodiment is a LED. In other not shown embodiments of the PPG apparatus 100, the light source is a laser source, in particular a laser diode.

The beam angle adapter 120 in this embodiment of the PPG apparatus 100 is a liquid crystal lens.

The PPG sensor 140 in this embodiment is a photodiode. In other not shown embodiments of the PPG apparatus 100, the PPG sensor is a video camera.

In a further not shown embodiment of the PPG apparatus 100, at least two light sources are used with different characteristic wavelengths, which enable a user of the PPG apparatus 100 to measure oxygen saturation of the external object 130, due to different absorption characteristics of oxygenated and deoxygenated hemoglobin.

The external object 130 does not form a part of the claimed PPG apparatus 100. The external object 130 is the object which is to be investigated by the PPG apparatus and thus can be changed arbitrarily. Non-limiting examples of external objects 130 are elastic tubes, animals, and human beings, or parts thereof.

In a further not shown embodiment, the PPG apparatus 100 is arranged in such a way that the external object 130 is between the beam angle adapter 120 and the PPG sensor 140. Thus, in this embodiment the scattered source light 150 has been scattered by passing through a part of the external object 130.

The AC signal component of the sensor signal is indicative of changes in time of the amount of scattered source light and therefore allows determining changes of the volume or the surface of the external object or both. Thus, in a non-limiting application, the PPG apparatus can output an AC signal component of the sensor signal indicative of vital sign information of the external object, for example a human being, such as respiratory rate, pulse rate and blood pressure. Due to different absorption characteristics of oxygenated and deoxygenated hemoglobin, oxygen saturation can be measured with the PPG apparatus, too.

Figure 2:
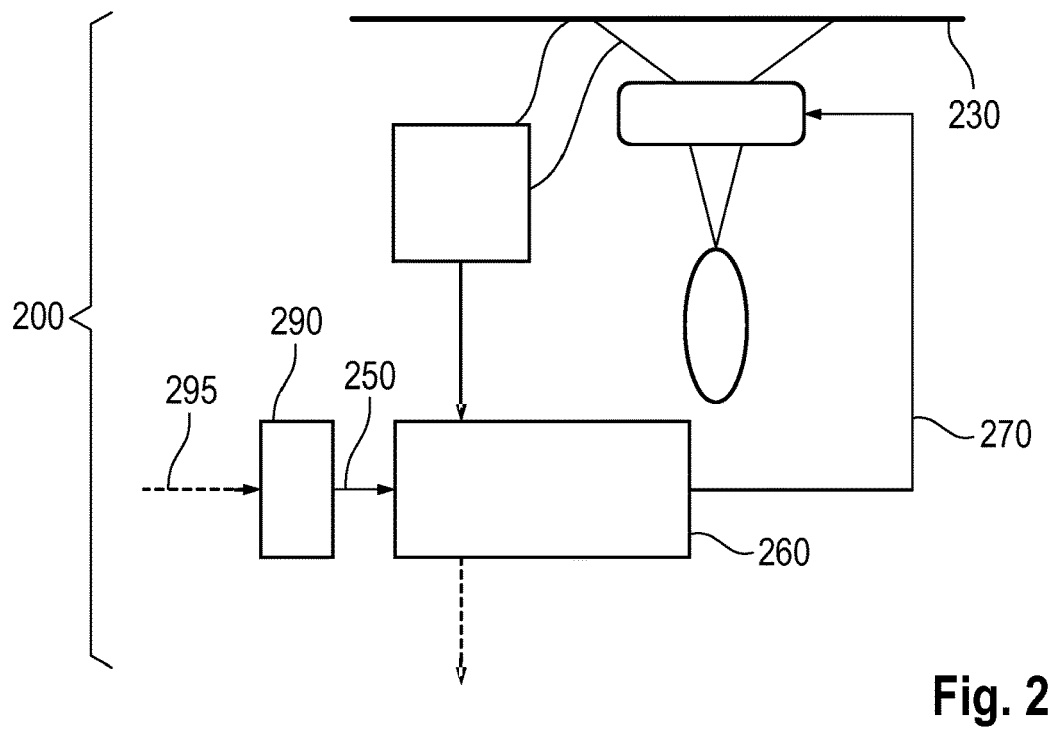
FIG. 2 shows a block diagram of an embodiment of a PPG apparatus with a user input interface.

FIG. 2 shows a simplified block diagram of an embodiment of a PPG apparatus 200 with a user input interface 290.

While all other components of the PPG apparatus 200 are arranged and configured in the same way as within the PPG apparatus 100 illustrated in FIG. 1, the PPG evaluation and control unit 260 is further configured to receive beam-angle control information 250 as a user input 295 via a user input interface 290 of the PPG apparatus 200 and to determine and provide the beam-angle control signal 270 in dependence on the beam-angle control information 250.

In this embodiment of the PPG apparatus 200, the user input 295 is indicative of a parameter of the external object 230.

The user input interface 290 in this embodiment is a stationary computer. In other not shown embodiments, the user input interface is a mobile phone, a notebook computer, a computer watch device, or a convertible or tablet computer.

Figure 3:
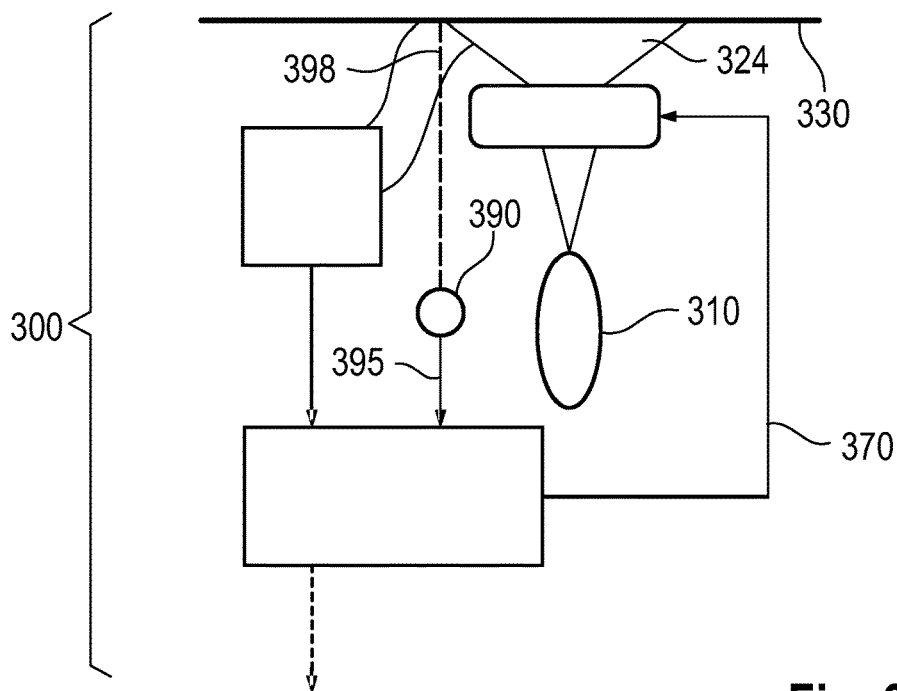
FIG. 3 shows a block diagram of an embodiment of a PPG apparatus with a distance sensor.

FIG. 3 shows a simplified block diagram of an embodiment of a PPG apparatus 300 with a distance sensor 390.

The PPG apparatus 300 works as the PPG apparatus 100 illustrated in FIG. 1, with the only difference that the distance sensor 390 is configured to provide a distance signal 395 which is indicative of a distance between the light source 310 and the external object 330. Furthermore, the PPG evaluation and control unit 360 is configured to receive the distance signal 395 and to determine and provide the beam-angle control signal 370 in dependence on the received distance signal 395.

In this embodiment of the PPG apparatus 300, the distance sensor 390 determines the distance by a time-of-flight measurement concerning a beam of light 398 provided by the distance sensor 390. Furthermore, an increasing distance between the light source 310 and the external object 330 leads to a decreasing modified beam angle 324 and to a corresponding beam-angle control signal 370. Analogously, a decreasing distance between the light source 310 and the external object 330 leads to an increasing modified beam angle 324.

Figure 4:
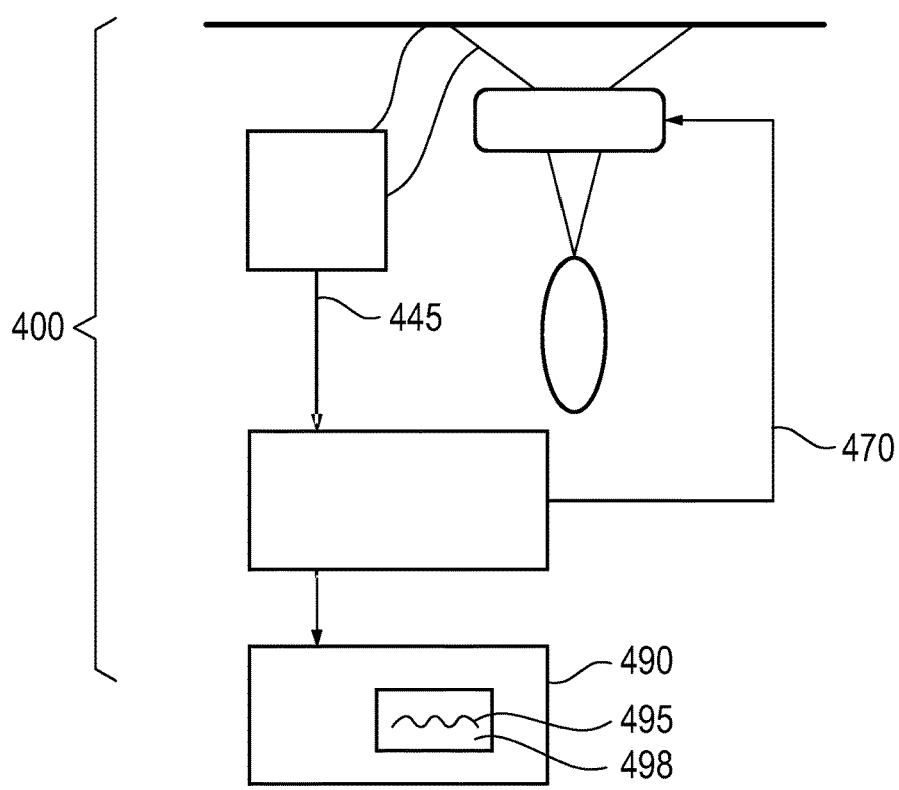
FIG. 4 shows a block diagram of an embodiment of a PPG apparatus with a user output interface.

FIG. 4 shows a simplified block diagram of an embodiment of a PPG apparatus 400 with a user output interface 490.

While all other components are arranged and configured in the same way as in the PPG apparatus 100 illustrated in FIG. 1, the PPG apparatus 400 comprises an output interface 490 which is configured to provide an output 495 indicative of the AC signal component of the sensor signal 445, or of a DC signal component of the sensor signal 445, or of the beam-angle control signal 470. In this embodiment of the PPG apparatus 400, the output 495 is a graphical signal on a display 498 of the output interface 490.

In another not shown embodiment of the PPG apparatus, the output is an acoustic signal.

Figure 5:
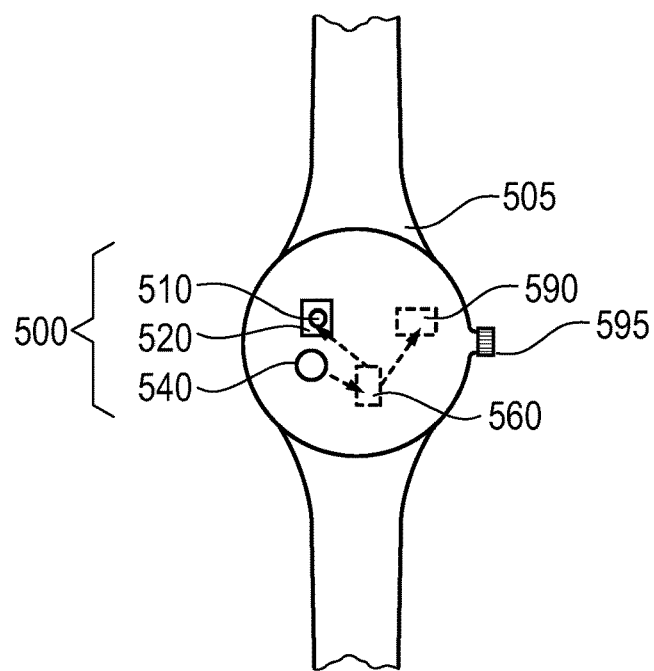
FIG. 5 is a schematic illustration of an embodiment of a PPG apparatus provided within the encasement of a sport watch.

FIG. 5 is a schematic illustration of an embodiment of a PPG apparatus 500 provided within the encasement 505 of a computer watch device.

The PPG apparatus 500 is similar to the PPG apparatus 400 shown in FIG. 4. The light source 510 is arranged behind the beam angle adapter 520. The adjacent PPG sensor 540 is connected to the PPG evaluation and control unit 560 which in turn is connected to the beam angle adapter 520 and to the user output interface 590 with its display.

In case of usage, a user would wear the computer watch device with its encasement 505 at the wrist. The beam of source light provided by the light source 510 would pass the beam angle adapter 520 and thereby the source beam angle would be modified. The resulting beam of source light with the modified beam angle would be scattered at the arm of the user and the PPG sensor 540 would be provided with the scattered source light. The PPG sensor 540 would provide a sensor signal which would be received by the PPG evaluation and control unit 560. There, an output would be determined and provided to be received by the user output interface 590.

The connection between PPG evaluation and control unit 560 and the beam angle adapter 520 is used to provide the beam-angle control signal for changing the modified beam angle. In this embodiment, the beam-angle control signal is determined by the PPG evaluation and control unit 560 by determining a ratio difference between a ratio of the AC signal component of the sensor signal and the DC signal component of the sensor signal and a predetermined reference ratio thereof. This determining is implemented in the following way:
the ratio difference is determined and the modified beam-angle is increased by a certain angle change;
the ratio difference is determined and if the ratio difference is larger than before, the beam-angle is decreased by an angle larger than the certain angle change.

These steps are repeated by the PPG apparatus 500 until the ratio difference is smaller than a predetermined limit. Thus a ratio of the AC signal component of the sensor signal and the DC signal component of the sensor signal which is close to the reference ratio can be reached without any input by the user.

In a further not shown variant of this embodiment of the PPG apparatus 500, the PPG apparatus comprises a pressure sensor, which is configured to provide a pressure signal which is indicative of a pressure exerted by the PPG apparatus 500 on the wrist of the user. In this variant of the PPG apparatus 500, the PPG evaluation and control unit 560 is further configured to receive the pressure signal and to determine and provide the beam-angle control signal in dependence on the received pressure signal.

In a further not shown variant of this embodiment of the PPG apparatus 500, a touch screen (not shown) or a button 595, here in the shape of a winder is integrated in the encasement 505 of the computer watch device, and is configured to provide a user input signal which is received by the PPG evaluation and control unit 560. In this variant, the PPG evaluation and control unit 560 is configured to determine and provide the beam-angle control signal in dependence on the user input signal.

Figure 6:
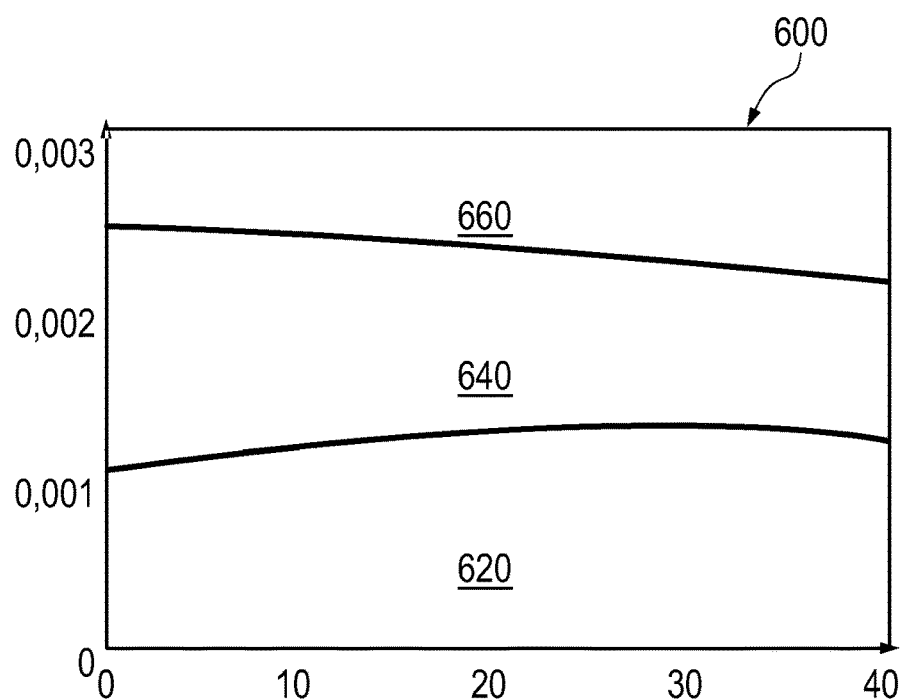
FIG. 6 is an illustration of an object-type classification of an embodiment of a PPG apparatus.

FIG. 6 is an illustration of an object-type classification 600 of an embodiment of a PPG apparatus.

The object-type classification 600 allocates different amounts of the DC signal component of the sensor signal, which are given at the y-axis as ratio between DC power emitted by the light source and DC power received by the PPG sensor, in dependence on the modified beam angle of the PPG apparatus, given at the x-axis in degree.

In this embodiment, a calibration measurement consists of the determining of the DC signal component of the sensor signal for a certain modified beam angle. The determined point within the object-type classification 600 defines whether the external object has the object type 620, the object type 640 or the object type 660, which are, in this embodiment, different skin colors, while the external object is a human being. Object type 660 represents lighter skin color than object type 640, and object type 640 represents a lighter skin color than object type 620. Since the DC signal component of the sensor signal includes a source light intensity received by the PPG sensor, the DC signal component of the sensor signal can be used as a control measure in order to determine whether or not a sufficient amount of scattered source light reaches the PPG sensor.

In a further embodiment of the PPG apparatus, the information concerning the determined object type is used by the PPG evaluation and control unit to determine and provide the beam-angle control signal in dependence on the determined object type.

In another not shown embodiment, an allocation of a signal-component ratio of the AC signal component of the sensor signal and the DC signal component of the sensor signal to an object type is used for the object-type classification.

Figure 7:
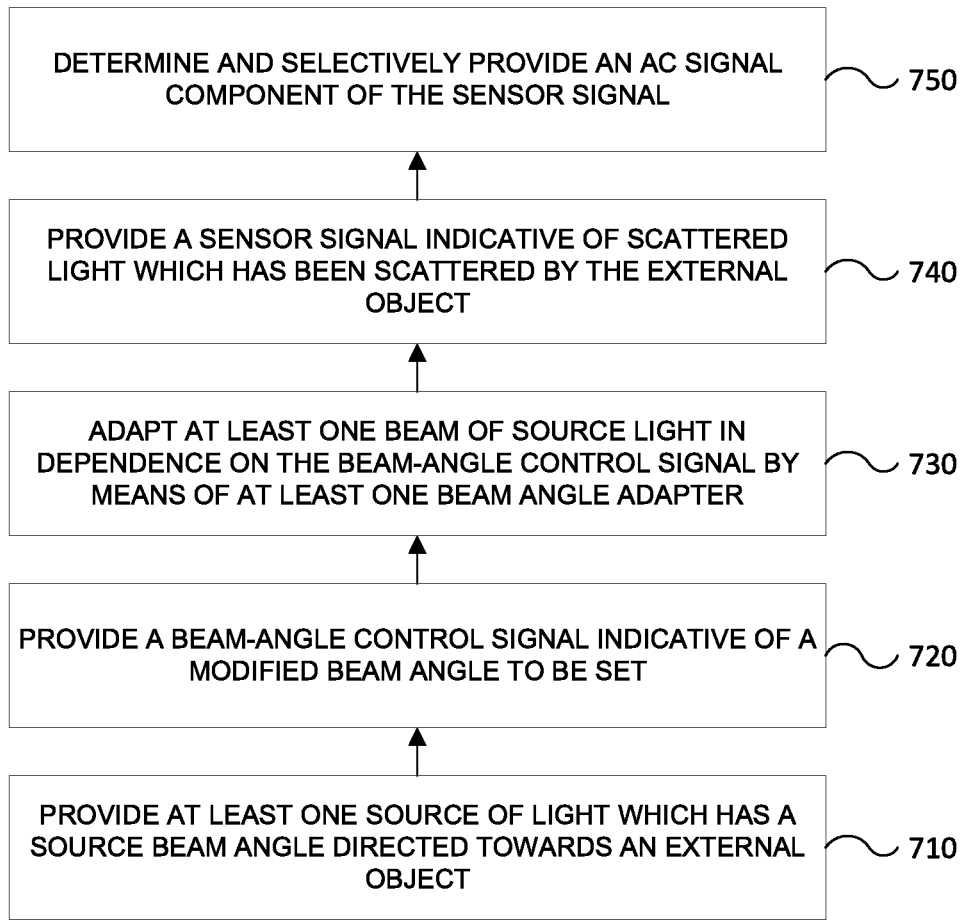
FIG. 7 is a flow diagram that illustrates an embodiment of a method for operating a PPG apparatus.

FIG. 7 is a flow diagram that illustrates an embodiment of a method for operating a PPG apparatus.

In the method at least one beam of source light is provided which has a source beam angle directed towards an external object (step 710).

The PPG apparatus provides a beam-angle control signal indicative of a modified beam angle to be set, which differs from the source beam angle of the at least one beam of source light (step 720).

The at least one beam of source light is adapted in dependence on the beam-angle control signal to set the modified beam angle by means of at least one beam angle adapter (step 730).

In a subsequent step 740, a sensor signal is provided indicative of scattered source light, which has been scattered by the external object.

After that, an AC signal component of the sensor signal is determined and selectively provided (step 750).

Figure 8:
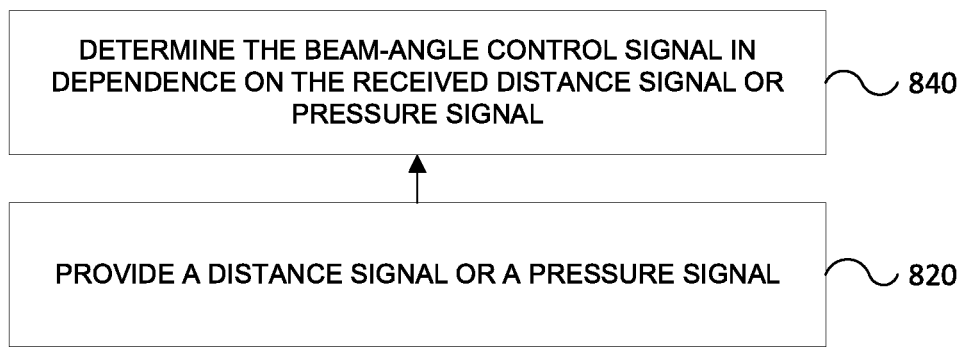
FIG. 8 is a flow diagram that illustrates an embodiment of a method for operating a PPG apparatus.

FIG. 8 is a flow diagram that illustrates an embodiment of a method for operating a PPG apparatus.

The method comprises the providing of a distance signal which is indicative of a distance between the light source and the external object or of a pressure signal which is indicative of a pressure exerted by the PPG apparatus on the external object (step 820).

In the following step 840, the distance signal or the pressure signal is received and the beam-angle control signal is determined and provided in dependence on the received distance signal or pressure signal.

A variant of this embodiment comprises the receiving of the distance signal and of a distance control signal and afterwards the modifying of the distance between the light source and the external object in dependence on the distance control signal and on the distance signal.

Figure 9:
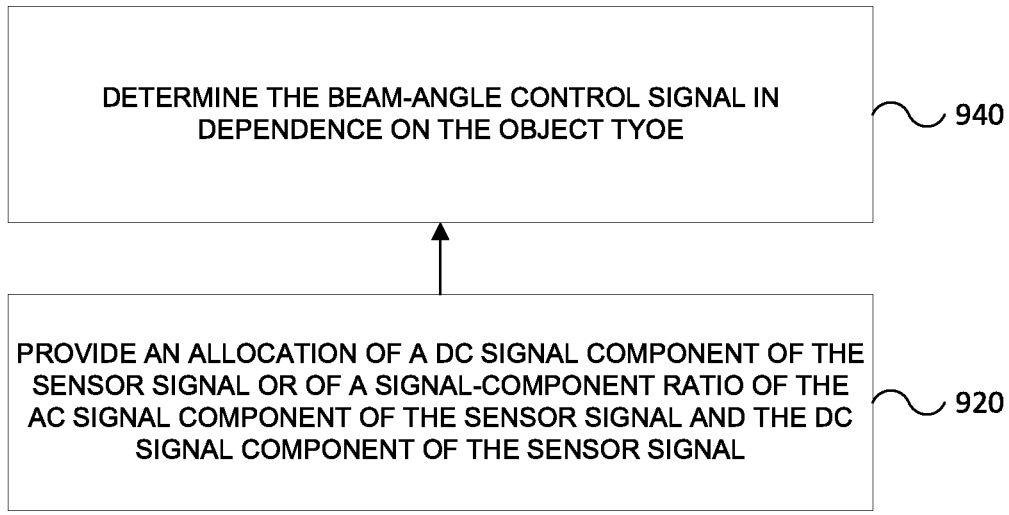
FIG. 9 is a flow diagram that illustrates an embodiment of a method for operating a PPG apparatus.

FIG. 9 is a flow diagram that illustrates an embodiment of a method for operating a PPG apparatus.

The method comprises as a first step 920 the providing of an allocation of a DC signal component of the sensor signal or of a signal-component ratio of the AC signal component of the sensor signal and the DC signal component of the sensor signal to an object type by a predetermined object-type classification of external objects. The object-type classification allocates different amounts of the DC signal component or of the signal-component ratio to different object types.

The second step 940 comprises the determining of the beam-angle control signal in dependence on the object type determined by the allocation.

Figure 10:
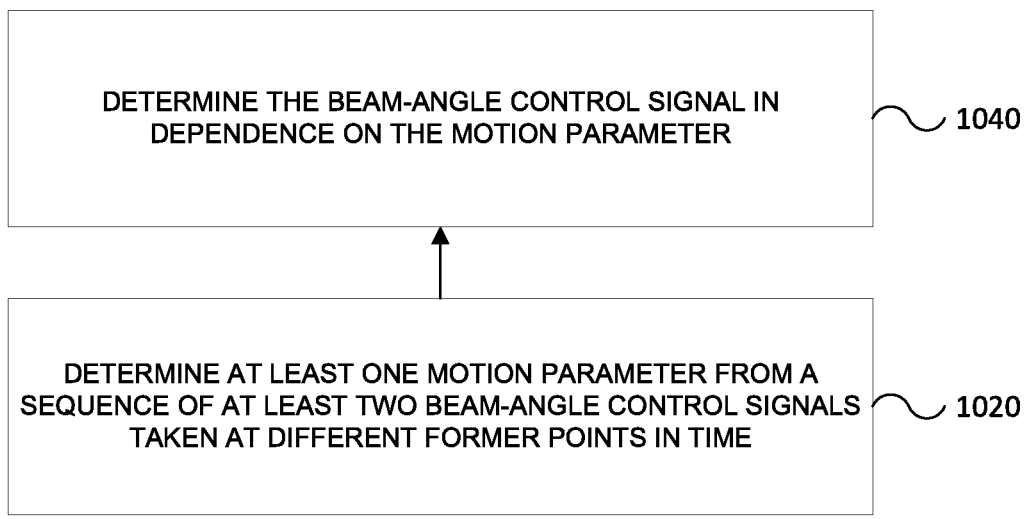
FIG. 10 is a flow diagram that illustrates an embodiment of a method for operating a PPG apparatus.

FIG. 10 is a flow diagram that illustrates an embodiment of a method for operating a PPG apparatus.

The method comprises the determining of at least one motion parameter indicative of a motion of the external object as a whole relative to the light source from a sequence of at least two beam-angle control signals taken at different former points in time (step 1020).

Afterwards the beam-angle control signal is determined in dependence on the motion parameter (step 1040).

In a variant of this embodiment, the at least two beam angle control signals are indicative of the distance between the light source and the external object at different former points in time. Thus, in this variant, the motion of the external object into the direction of the beam of source light is estimated.

In a further variant of this embodiment, the at least two beam angle control signals are indicative of the acceleration of the PPG apparatus at different former points in time.

In summary, the invention relates to a photoplethysmography (PPG) apparatus, comprising at least one light source configured to generate a beam of source light having a source beam angle and at least one controllable beam angle adapter arranged between the light source and the external object and configured to receive a beam-angle control signal indicative of a modified beam angle to be set, the beam angle adapter being further configured to receive the beam of source light having the source beam angle and to provide the beam of source light with the a modified beam angle to an external object. The PPG apparatus further comprises at least one PPG sensor which is arranged and configured to provide a sensor signal indicative of scattered source light, which has been scattered by the external object and detected by the PPG sensor, and a PPG evaluation and control unit, which is configured to receive the sensor signal, to provide the beam-angle control signal and to determine and selectively provide at its output an AC signal component of the sensor signal.

While the present invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In particular the invention is not restricted to the use of liquid crystal lenses or monochromatic light sources. The invention is furthermore not restricted to medical applications.

In the claims, the word "comprising" does not exclude other elements or steps, and the indefinite article "a" or "an" does not exclude a plurality.

A single step or other units may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A photoplethysmography (PPG) apparatus comprising:
   at least one light source configured to generate a beam of source light having a source beam angle directed towards an external object;
   at least one controllable beam angle adapter configured to be between the light source and the external object and configured to receive a beam-angle control signal indicative of a modified beam angle to be set, which differs from the source beam angle, the beam angle adapter being further configured to receive the beam of source light having the source beam angle and to provide the beam of source light with the modified beam angle to the external object;
   at least one PPG sensor which is configured to provide a sensor signal indicative of scattered source light, which has been scattered by the external object and detected by the PPG sensor, and which comprises an AC signal component indicative of a change of an amount of blood or air in a body part and which allows determination of vital sign information of the external object; and
   a PPG evaluation and control unit, which is configured to receive the sensor signal, to determine the modified beam angle based on the AC signal component of the sensor signal or based on both the AC signal component of the sensor signal and a DC signal component of the sensor signal, to determine and provide the beam-angle control signal based on the modified beam angle, and to determine and selectively provide at its output the AC signal.

2. The PPG apparatus of claim 1, wherein the beam angle adapter comprises a liquid crystal lens with an adjustable focal length.

3. The PPG apparatus of claim 1, wherein the PPG evaluation and control unit is configured to determine a ratio difference between a ratio of the AC signal component of the sensor signal and the DC signal component of the sensor signal and a predetermined reference ratio thereof, and to provide the beam-angle control signal in dependence on the ratio difference.

4. The PPG apparatus of claim 1, further comprising a distance sensor, which is configured to provide a distance signal which is indicative of a distance between the light source and the external object, wherein the PPG evaluation and control unit is configured to receive the distance signal and to determine and provide the beam-angle control signal in dependence on the received distance signal.

5. The PPG apparatus of claim 1, further comprising a pressure sensor, which is configured to provide a pressure signal which is indicative of a pressure exerted by the PPG apparatus on the external object, wherein the PPG evaluation and control unit is configured to receive the pressure signal and to determine and provide the beam-angle control signal in dependence on the received pressure signal.

6. The PPG apparatus of claim 1, wherein the PPG evaluation and control unit is further configured to receive beam-angle control information as a user input via a user input interface of the PPG apparatus and to determine and provide the beam-angle control signal in dependence on the beam-angle control information.

7. The PPG apparatus of claim 1, wherein the PPG evaluation and control unit is configured to control performance of a calibration measurement by the PPG apparatus to provide a calibration of the PPG apparatus,
   the calibration providing an assignment of
   a) the DC signal component of the sensor signal or
   b) a signal-component ratio of the AC signal component of the sensor signal and the DC signal component of the sensor signal,
   to an object type, the object type comprising a predetermined object-type classification of external objects, the object-type classification assigning different amounts of the DC signal component or of the signal-component ratio to different object types.

8. The PPG apparatus of claim 7, wherein the PPG evaluation and control unit is configured to determine the object type based on the sensor signal and the calibration, and to determine the beam-angle control signal in dependence on the object type.

9. The PPG apparatus of claim 1, wherein the PPG evaluation and control unit is further configured to determine at least one motion parameter indicative of a motion of the external object as a whole relative to the light source, and to determine the beam-angle control signal in dependence on the motion parameter.

10. A method for operating a photoplethysmography (PPG) apparatus the method comprising:
   providing at least one beam of source light having a source beam angle directed towards an external object;
   determining and providing a beam-angle control signal indicative of a modified beam angle to be set, which differs from the source beam angle of the at least one beam of source light;

adapting the at least one beam of source light in dependence on the beam-angle control signal to set the modified beam angle by means of at least one beam angle adapter;

providing a sensor signal indicative of scattered source light, which has been scattered by the external object, and which comprises an AC component indicative of a change of an amount of blood or air in a body part and which allows determination of vital sign information of the external object; and determining and selectively providing the AC signal component of the sensor signal; wherein determining and providing the beam-angle control signal is performed in dependence on determining the modified beam angle based on both the AC signal component of the sensor signal and a DC signal component of the sensor signal.

11. The method of claim 10, further comprising:

providing a distance signal which is indicative of a distance between a light source and the external object or a pressure signal which is indicative of a pressure exerted by the PPG apparatus on the external object;

receiving the distance signal or the pressure signal and determining and providing the beam-angle control signal in dependence on the received distance signal or pressure signal.

12. The method of claim 10, further comprising:

providing an assignment of
  a) the DC signal component of the sensor signal or
  b) a signal-component ratio of the AC signal component of the sensor signal and the DC signal component of the sensor signal,
  to an object type, the object type comprising a predetermined object-type classification of external objects, the object-type classification assigning different amounts of the DC signal component or of the signal-component ratio to different object types; and
  determining the beam-angle control signal in dependence on the object type determined by the assignment.

13. The method of claim 10, further comprising:

determining from a sequence of at least two beam-angle control signals taken at different former points in time at least one motion parameter indicative of a motion of the external object as a whole relative to the light source; and determining the beam-angle control signal in dependence on the motion parameter.

14. A photoplethysmography (PPG) apparatus comprising:

at least one light source configured to generate a beam of source light having a source beam angle directed towards an external object;

at least one controllable beam angle adapter configured to be between the light source and the external object and configured to receive a beam-angle control signal indicative of a modified beam angle to be set, which differs from the source beam angle, the beam angle adapter being further configured to receive the beam of source light having the source beam angle and to provide the beam of source light with the modified beam angle to the external object;

at least one PPG sensor which is configured to provide a sensor signal indicative of scattered source light, which has been scattered by the external object and detected by the PPG sensor, and which comprises an AC signal component indicative of a change of an amount of blood or air in a body part and which allows determination of vital sign information of the external object; and a PPG evaluation and control unit, which is configured to receive the sensor signal, to determine and provide the beam-angle control signal in dependence on the AC signal component of the sensor signal or in dependence on the AC signal component of the sensor signal and a DC signal component of the sensor signal and to determine and selectively provide at its output the AC signal;

wherein the PPG evaluation and control unit is configured to determine a ratio difference between a ratio of the AC signal component of the sensor signal and the DC signal component of the sensor signal and a predetermined reference ratio thereof, and to provide the beam-angle control signal in dependence on the ratio difference.

* * * * *